(12) United States Patent
Sweet et al.

(10) Patent No.: US 9,354,203 B2
(45) Date of Patent: May 31, 2016

(54) HYDROSHOCK INSPECTION SYSTEM

(71) Applicant: The Boeing Company, Chicago, IL (US)

(72) Inventors: William J. Sweet, Seattle, WA (US); Kevin Richard Housen, Tacoma, WA (US); Richard Henry Bossi, Renton, WA (US)

(73) Assignee: THE BOEING COMPANY, Chicago, IL (US)

( * ) Notice: Subject to any disclaimer, the term of this patent is extended or adjusted under 35 U.S.C. 154(b) by 370 days.

(21) Appl. No.: 13/762,763

(22) Filed: Feb. 8, 2013

(65) Prior Publication Data

US 2014/0224020 A1 Aug. 14, 2014

(51) Int. Cl.
*G01N 29/04* (2006.01)
*G01N 29/22* (2006.01)
*G01N 29/24* (2006.01)

(52) U.S. Cl.
CPC .............. *G01N 29/04* (2013.01); *G01N 29/045* (2013.01); *G01N 29/225* (2013.01); *G01N 29/2418* (2013.01); *G01N 2291/0231* (2013.01); *G01N 2291/02827* (2013.01); *G01N 2291/2694* (2013.01)

(58) Field of Classification Search
CPC .............................. G01N 29/04; G01N 29/045
USPC .................................................. 73/588, 644
See application file for complete search history.

(56) References Cited

U.S. PATENT DOCUMENTS

| | | | | |
|---|---|---|---|---|
| 3,497,728 A | * | 2/1970 | Ostrofsky et al. | ................ 73/644 |
| 3,835,954 A | * | 9/1974 | Layotte | .......................... 181/116 |
| 4,147,064 A | * | 4/1979 | Bond | .............................. 73/596 |
| 5,616,865 A | * | 4/1997 | Webster | .......................... 73/627 |
| 5,743,862 A | | 4/1998 | Izumi | |
| 6,848,321 B2 | | 2/2005 | Bossi et al. | |
| 7,410,464 B2 | * | 8/2008 | Ein-Gal | ................. G10K 11/30 362/341 |

FOREIGN PATENT DOCUMENTS

| | | |
|---|---|---|
| JP | H03280941 A | 12/1991 |
| JP | H1078419 A | 3/1998 |
| JP | 2001264302 A | 9/2001 |
| JP | 2005300273 A | 10/2005 |

OTHER PUBLICATIONS

Bossi et al., "Bonding Primary Aircraft Structure: The Issues," Manufacturing Engineering, vol. 146, No. 3, Mar. 2011, pp. 101-109.

(Continued)

*Primary Examiner* — John Chapman, Jr.
(74) *Attorney, Agent, or Firm* — Yee & Associates, P.C.

(57) ABSTRACT

A method and apparatus for testing a test object. A stress wave is generated in a fluid within a cavity in a structure. The stress wave is directed through the fluid within the cavity into the test object.

19 Claims, 11 Drawing Sheets

(56) References Cited

OTHER PUBLICATIONS

Bossi et al., "Laser Bond Testing," Materials Evaluation, vol. 67, No. 7, Jul. 2009, pp. 819-827.
Bossi et al., "Using Shock Loads to Measure Bonded Joint Strength," Materials Evaluation, May 2002, 14 pages.
Bossi et al., "Laser Bond Inspection for Adhesive Bond Strength," SAMPE, May 2011, 10 pages.
Bossi et al., "Application of Stress Waves to Bond Inspection," SAMPE, May 2004, 14 pages.
"A Method of Detecting Weak Bond With Ultrasonic Shock Waves," IP.com IPCOM000216008D, Mar. 19, 2012, 3 pages.
Notice of Reasons for Rejection and English translation, dated Jan. 28, 2015, regarding Japanese Patent Application No. 2014-019039, 4 pages.
Notice of Reasons for Rejection and English translation, issued Nov. 4, 2015, regarding Japanese Patent Application No. 2014-019039, 5 pages.

* cited by examiner

HYDROSHOCK INSPECTION SYSTEM

BACKGROUND INFORMATION

1. Field

The present disclosure relates generally to testing objects and, in particular, to testing the strength of bonds and objects. Still more particularly, the present disclosure relates to a method and apparatus for testing the strength of bonds in a bonded structure using tension waves.

2. Background

A composite object may be comprised of one or more composite structures that are bonded to each other. The composite object is often required to withstand loads that may be encountered during normal or even abnormal use of the composite object. As a result, identifying the strength of bonds in the composite object nondestructively may be required to assess that the composite object is capable of withstanding those forces.

Nondestructive testing or Non-destructive testing (NDT) is a wide group of analysis techniques used in science and industry to evaluate the properties of a material, component or system without causing damage. Because NDT does not permanently alter the article being inspected, it is a highly valuable technique that can save both money and time in product evaluation, troubleshooting and research.

Nondestructive testing of the composite object is more desirable. If the bonds in the composite object meet the desired standard, the composite object remains useable. Nondestructive evaluations are typically selected to fit specific bond material rather than general testing for all parameters. For example, laser bond inspection is a method currently used for nondestructive evaluations of bonds in composite objects. Laser bond inspection tests the strength of bonds between composite structures within a composite object. In this technique, weak bonds may be "pulled apart" by tension waves traveling through the structure. Existing bond inspection devices have multiple draw backs including the fact that they are expensive to construct and operate, and their large footprint makes it difficult to inspect bonds with certain shapes.

Further, inspecting bonds on composite objects such as installed parts on an aircraft may be more difficult than desired because of the size and limited reach of these types of laser bond inspection systems. For example, parts with narrow flanges or angles may preclude placement of the laser bond inspection head in a location to perform the inspection.

Therefore, it would be desirable to have a method and apparatus that takes into account at least some of the issues discussed above, as well as other possible issues.

SUMMARY

In one illustrative embodiment, a method for testing a test object is presented. A stress wave is generated in a fluid within a cavity in a structure. The stress wave is directed through the fluid within the cavity into the test object.

In another illustrative embodiment, an apparatus comprises an energy source and a structure. The structure has a cavity configured to hold a fluid. The energy source is configured to generate a stress wave that travels through the fluid within the cavity into a test object.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

With laser bond inspection, a laser beam is directed at the front surface of a composite object. The laser beam creates mechanical waves in the form of stress waves that travel through the composite object toward the back surface of the composite object. When the stress wave reaches a back surface of the object under test, the stress wave is reflected back from that surface producing a tension wave that propagates back toward the front surface of the object. The tension waves apply tension to the internal structure of the object, including any bond lines between the front and back surface of the object. The tension waves may have a sufficient strength that is selected to determine whether bonds between the parts of the object have a desired strength.

Laser bond inspection may be considered a nondestructive testing method when the bonds between composite structures are sufficiently strong. If a tension wave encounters a bond within the composite object that has the desired strength, the bond remains intact and inconsistencies are absent. The composite object may be examined to determine whether any inconsistencies are present in the composite object. If the bond is sufficiently strong, the composite object is not altered and may be used in different applications. This composite object also may be certified as providing a selected strength value.

If the tension wave encounters a bond within the composite object that does not have the desired strength, an inconsistency may occur. If an inconsistency is present, the composite object does not have the desired strength and may be discarded, reworked, or otherwise processed.

Illustrative embodiments recognize and take into account one or more different considerations. For example, those embodiments recognize and take into account that stress waves may be generated using mechanisms other than a laser beam directed towards a test object. For example, the illustrative embodiments recognize and take into account that a stress wave may be generated through a fluid that is coupled to the test object.

One or more of the illustrative embodiments may employ a hydroshock technique to generate a stress wave. In one illustrative example, a stress wave is generated in a fluid within a cavity of a structure. The stress wave is directed through the fluid and the cavity into a test object. In one illustrative example, the structure with the cavity may take the form of a tube or cylinder.

Figure 1:
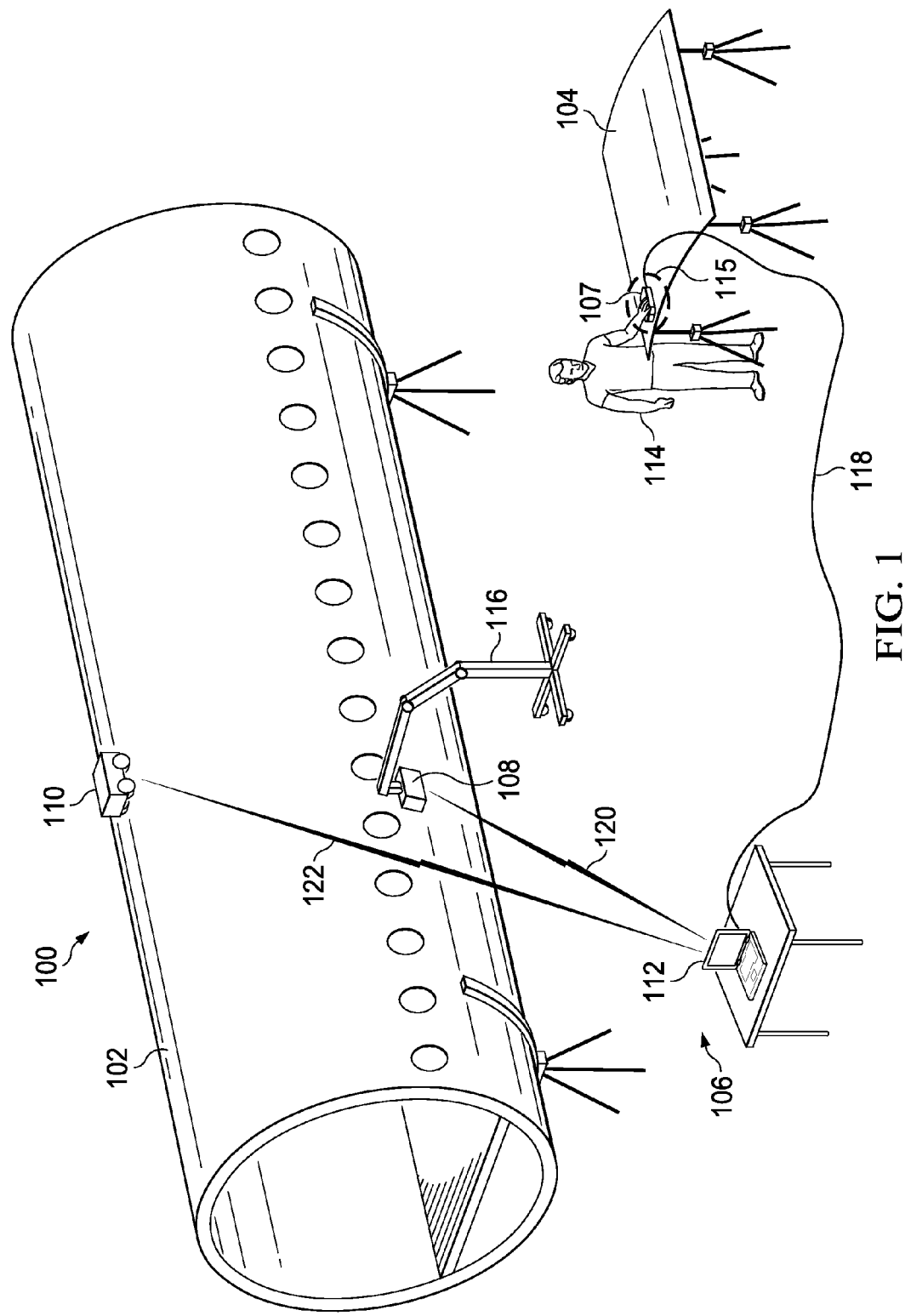
FIG. 1 is an illustration of an inspection environment in accordance with an illustrative embodiment.

With reference now to the figures and in particular, with reference to FIG. 1, an illustration of an inspection environment is depicted in accordance with an illustrative embodiment. Inspection environment 100 is an example of one environment in which an illustrative embodiment may be implemented.

In this illustrative example, fuselage 102 and skin panel 104 are examples of composite objects. These composite objects may be comprised of composite structures that are bonded to each other. In these illustrative examples, an inspection of these bonds in fuselage 102 and skin panel 104 may be made in accordance with an illustrative embodiment.

In this illustrative example, inspection system 106 is configured to inspect the bonds in fuselage 102 and skin panel 104. As depicted, inspection system 106 includes inspection unit 107, inspection unit 108, inspection unit 110, and computer 112.

In this illustrative example, inspection unit 107 is a portable inspection unit operated by operator 114. Operator 114 may place inspection unit 107 at a location on skin panel 104. Operator 114 may then move a distance away from inspection unit 107. This distance may be a distance that has been determined to be safe during operation of inspection unit 107. Inspection unit 107 may then operate to perform inspection of bonds within skin panel 104.

After the inspection of the bonds within skin panel 104 has taken place at the location that inspection unit 107 was placed by operator 114, operator 114 may return to inspection unit 107 and move inspection unit 107 to another location on skin panel 104.

In other illustrative examples, operator 114 may remain at the location or may hold inspection unit 107 during inspection of the bonds within skin panel 104 depending on the amount of energy generated by inspection unit 107 and the design of inspection unit 107. A more detailed illustration of inspection unit 107 in section 115 is found in the description of FIG. 4 below.

Inspection unit 108 takes the form of an end effector for robotic arm 116. Robotic arm 116 may move inspection unit 108 along fuselage 102 to perform inspections of bonds within fuselage 102.

As depicted, inspection unit 110 takes the form of a crawler. Inspection unit 110 may move on fuselage 102 to perform inspections of bonds within fuselage 102.

Information generated by inspection unit 107, inspection unit 108, and inspection unit 110 are sent to computer 112. Initially, computer 112 may send commands to inspection unit 107, inspection unit 108, and inspection unit 110 to control the operation of these inspection units. The information and commands are sent over communications link 118, communications link 120, and communications link 122 in this illustrative example. As depicted, communications link 118 is a wired communications link. Communications link 120 and communications link 122 are wireless communications links.

The illustration of inspection environment 100 is only provided as an example of one type of environment in which an illustrative embodiment may be used to test bonds. One or more illustrative embodiments may be implemented in inspection environment 100 to inspect other types of objects other than aircraft parts. For example, the illustrative embodiments may be applied to testing bonds in a test object that may be selected from one of parts for an automobile, a building, a completed aircraft, a part installed on an aircraft, and other suitable types of objects that may contain bonds for which testing is desirable.

Figure 2:
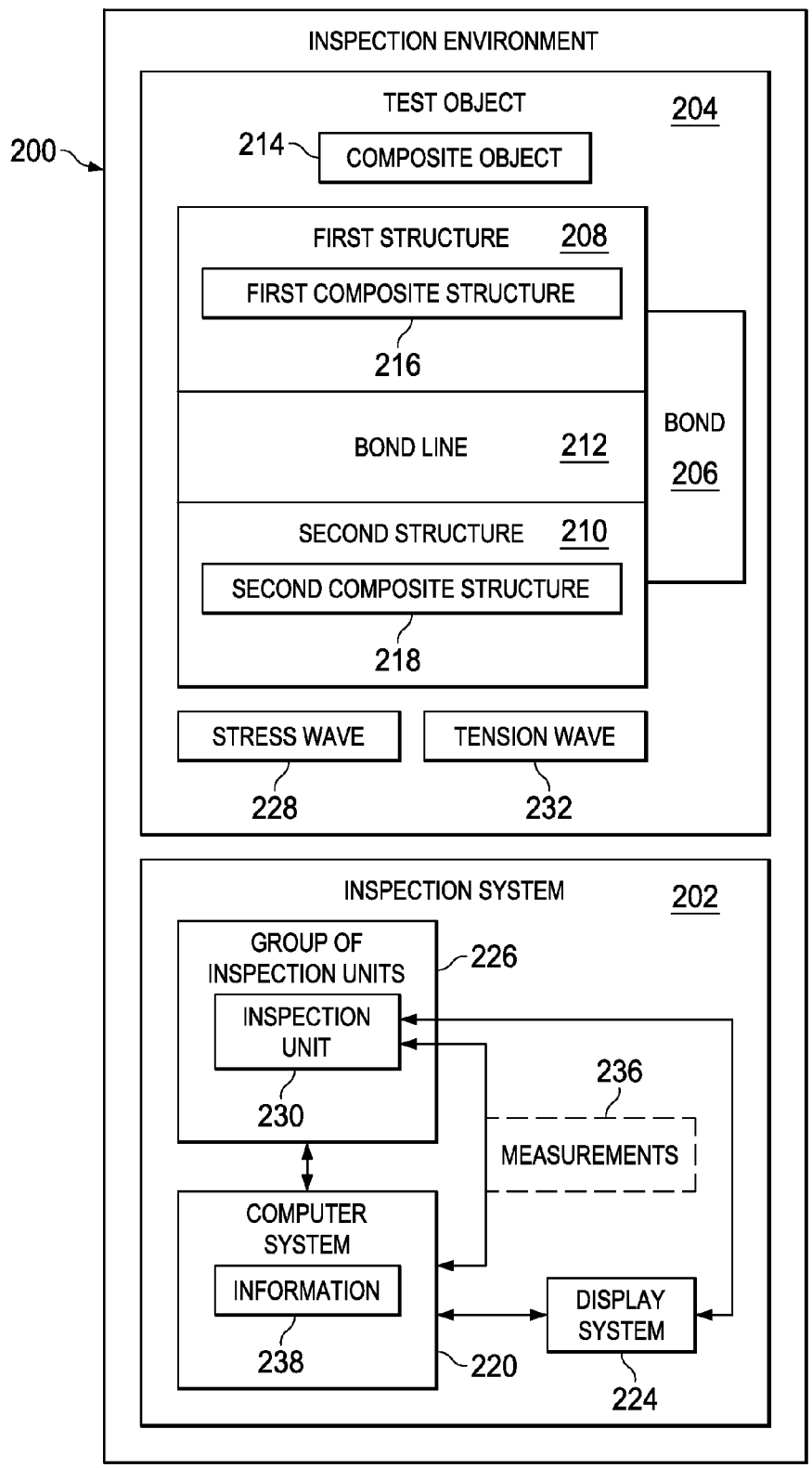
FIG. 2 is an illustration of a block diagram of an inspection environment in accordance with an illustrative embodiment.

Turning next to FIG. 2, an illustration of a block diagram of an inspection environment is depicted in accordance with an illustrative embodiment. Inspection environment 100 in FIG. 1 is an example of one implementation for inspection environment 200 shown in block form in FIG. 2.

As depicted, inspection environment 200 includes inspection system 202. Inspection system 202 is configured to test object 204. In particular, inspection system 202 is configured to test bond 206 in test object 204.

In this illustrative example, bond 206 is present where first structure 208 and second structure 210 are bonded to each other at bond line 212. Bond line 212 may be planar, nonplanar, or some combination thereof depending on the particular implementation.

In these illustrative examples, first structure 208 and second structure 210 may be bonded to each other in a number of different ways. For example, first structure 208 and second structure 210 may be bonded to each other using an adhesive.

Test object 204 may be comprised of any type of material. As depicted, test object 204 is composite object 214 in this illustrative example. Further, first structure 208 is first composite structure 216, and second structure 210 is second composite structure 218.

In this illustrative example, inspection system 202 includes computer system 220, display system 224, and group of inspection units 226. As used herein, a "group of," when used with reference items, means one or more items. For example, group of inspection units 226 is one or more inspection units.

Computer system 220 is configured to control the operation of group of inspection units 226. Computer system 220 is one or more computers. When more than one computer is present in computer system 220, those computers may communicate with each other using a communications medium such as a network.

In this illustrative example, stress wave 228 is generated by inspection unit 230 in group of inspection units 226 and directed into test object 204. In the illustrative example, stress wave 228 is a wave that has a compressive component. Additionally, stress wave 228 also may have a tensile component at the tail or end of the wave.

Inspection unit 230 is a hardware system in these illustrative examples. In the illustrative examples, stress wave 228 generates a force on test object 204.

Tension wave 232 is generated either as a part of stress wave 228 or when the compressive component of stress wave 228 encounters a boundary in test object 204. This boundary may be, for example, the back wall of the test object 204 or some other suitable interface that may be within test object 204. Tension wave 232 generates a force that applies tension to the internal structure of test object 204. For example, tension wave 232 may pull at least one of first structure 208 and second structure 210 away from each other at bond line 212. Tension wave 232 may result in a load that is applied to bond 206. In the illustrative example, this load may be localized. The load may be considered to be localized when the load is applied to a specific area of the test object. In other words, the load maybe applied to an area rather than spread out throughout the test object.

As depicted, inspection unit 230 is also configured to measure at least one of stress wave 228 and tension wave 232 in test object 204. As used herein, the phrase "at least one of," when used with a list of items, means different combinations of one or more of the listed items may be used and only one of each item in the list may be needed. For example, "at least one of item A, item B, or item C" may include, without limitation, item A or item A and item B. This example also may include item A, item B, and item C or item B and item C. In other examples, "at least one of" may be, for example, without limitation, two of item A, one of item B, and ten of item C; four of item B and seven of item C; and other suitable combinations. The item may be a particular object, thing, or a category. In other words, at least one of means any combination items and number of items may be used from the list but not all of the items in the list are required.

After stress wave 228 has been directed into test object 204 and tension wave 232 has traveled through test object 204, inspection unit 230 may make measurements 236 of test object 204. Inspection unit 230 may measure at least one of wave energy, front surface displacement or velocity, back-surface displacement or velocity, ultrasonic transmission, ultrasonic attenuation, and other suitable properties with respect to test object 204.

Inspection unit 230 may send measurements 236 made of test object 204 after stress wave 228 and tension wave 232 have traveled through test object 204 to computer system 220 for storage. As depicted, computer system 220 may store at least one of information 238 and measurements 236. In other illustrative examples, inspection unit 230 may store information 238, measurements 236, or both.

Display system 224 is a hardware system and may include one or more display devices. Display system 224 may be connected to computer system 220, inspection unit 230, or both of these systems. Display system 224 is configured to display information 238. Information 238 is based on measurements 236 of test object 204. In these illustrative examples, display system 224 may be, for example, selected from one of an oscilloscope, a tablet computer, a notebook computer, and a workstation.

Figure 3:
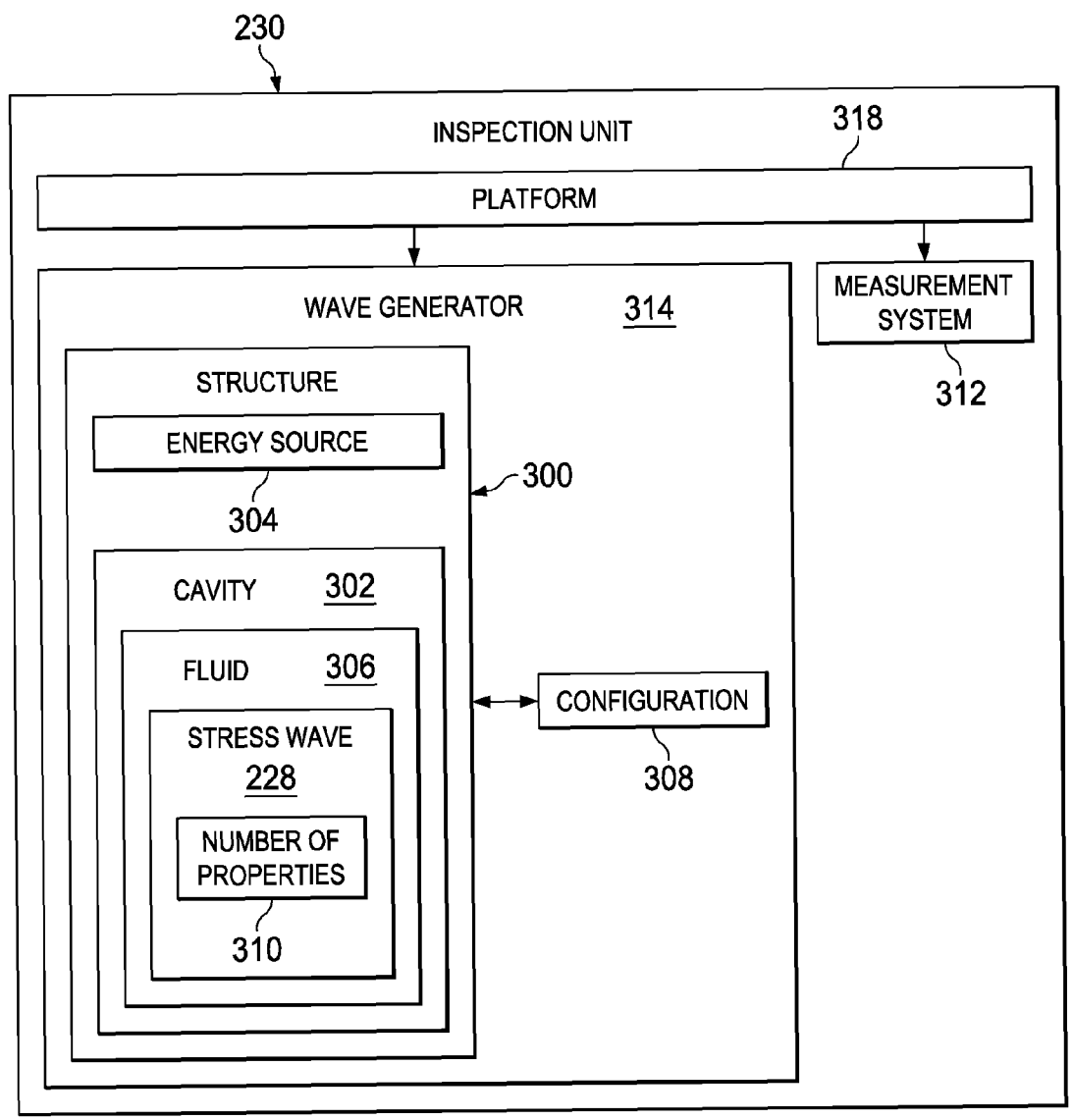
FIG. 3 is an illustration of a block diagram of an inspection unit in accordance with an illustrative embodiment.

With reference next to FIG. 3, an illustration of an inspection unit is depicted in accordance with an illustrative embodiment. In this depicted example, an example of components that may be found in inspection unit 230 in FIG. 2 is shown.

In this illustrative example, inspection unit 230 comprises a number of different components. In this depicted example, inspection unit 230 includes wave generator 314 and measurement system 312.

In this illustrative example, wave generator 314 in inspection unit 230 includes a number of different components. For example, wave generator in inspection unit 230 includes structure 300, cavity 302, and energy source 304.

Structure 300 may be any structure in which cavity 302 is configured to hold fluid 306 within cavity 302. Structure 300 may be comprised of any suitable material. For example, structure 300 may be comprised of a metal, plastic, titanium, steel, aluminum, polycarbonate, and other suitable materials.

In the illustrative example, structure 300 with cavity 302 has configuration 308. As depicted, cavity 302 is configured to direct stress wave 228 through fluid 306 in cavity 302 into test object 204 in FIG. 2. Fluid 306 may take various forms. For example, fluid 306 may be water, oil, and other suitable types of fluids.

Additionally, configuration 308 is selected to set number of properties 310 for stress wave 228. Number of properties 310 for stress wave 228 is set as stress wave 228 travels through cavity 302 into test object 204. As used herein, "a number of," when used with reference to items, means one or more items. For example, number of properties 310 is one or more properties. In the illustrative example, number of properties 310 is selected from at least one of a magnitude of stress wave 228, duration of stress wave 228, a rise time for stress wave 228, and the depth at which stress wave 228 is focused in the test object.

Measurement system 312 is a hardware system and is configured to measure at least one of stress wave 228 and tension wave 232 in test object 204 in FIG. 2. Measurement system 312 may take various forms. For example, measurement system 312 may be selected from at least one of a laser interferometer, a transducer system, and other suitable types of systems that may measure at least one of stress wave 228 and tension wave 232 while those waves travel within test object 204 in FIG. 2. The measurements may be surface displacements, surface velocities or internal material changes.

As depicted, wave generator 314 and measurement system 312 may be associated with platform 318. Platform 318 may take various forms such as a housing, a frame, an end effector, a crawler, or some other suitable type of platform. Of course, in some illustrative examples, wave generator 314 and measurement system 312 may be separate components.

The illustration of inspection environment 200 and the different components in FIGS. 2-3 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although only bond 206 is illustrated in the example in inspection environment 200 in FIG. 2, one or more additional bonds may be present in addition to or in place of bond 206. Further, test object 204 also may include one or more additional structures in addition to first structure 208 and second structure 210. These additional structures may or may not be composite structures depending on the particular implementation.

As another illustrative example, in some illustrative examples, measurement system 312 may be a separate component outside of inspection unit 230. In still other illustrative examples, the controller or processor also may be part of inspection unit 230. In yet another illustrative example, display system 224 may be included as part of inspection unit 230 in FIG. 2.

Figure 4:
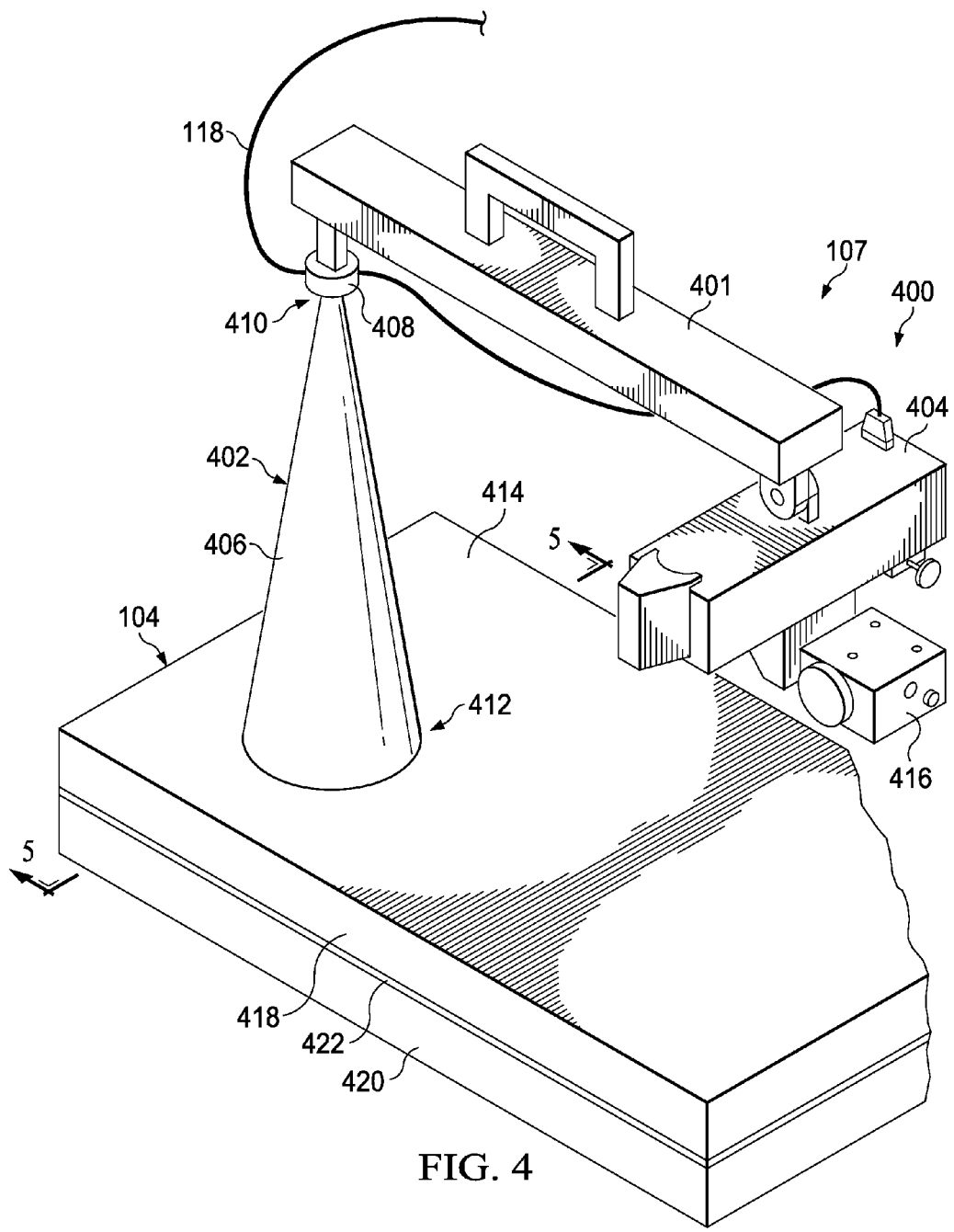
FIG. 4 is an illustration of a test setup in accordance with an illustrative embodiment.

Turning now to FIG. 4, an illustration of a test setup is depicted in accordance with an illustrative embodiment. In this depicted example, a more detailed illustration of inspection unit 107 operated by operator 114 from FIG. 1 is shown.

Also depicted in this view, inspection unit 107 includes a number of different components. For example, in inspection environment 400, inspection unit 107 includes frame 401, wave generator 402, and measurement unit 404.

As depicted, frame 401 is an example of one implementation for platform 318 shown in block form in FIG. 3. Frame 401 is a portable frame. Frame 401 may be moved from location to location by operator 114 to inspect skin panel 104.

Wave generator 402 and measurement unit 404 are associated with frame 401. When one component is "associated" with another component, the association is a physical association in the depicted examples. For example, a first component, wave generator 402, may be considered to be associated with a second component, frame 401, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

In this view, tube 406 and energy source 408 are shown. As depicted, tube 406 has a shape of a frustrum. Tube 406 is an example of a physical implementation for structure 300 shown in block form in FIG. 3. Additionally, tube 406 has first end 410 and second end 412.

Energy source 408 is configured to generate a stress wave. Energy source 408 is associated with first end 410. Second end 412 is configured to be placed on surface 414 of skin panel 104 in this illustrative example.

As depicted, measurement unit 404 is hardware and is configured to make measurements of waves within skin panel 104 that are generated by wave generator 402. Measurement unit 404 is an example of a physical implementation of measurement system 312 shown in block form in FIG. 3. In this illustrative example, measurement unit 404 takes the form of a laser interferometer 416.

As can be seen in this view, skin panel 104 is comprised of first composite structure 418 and second composite structure 420. These two composite structures are bonded to each other at bond line 422 in this illustrative example. Inspection unit 107 is used to test the bond between first composite structure 418 and second composite structure 420.

Figure 5:
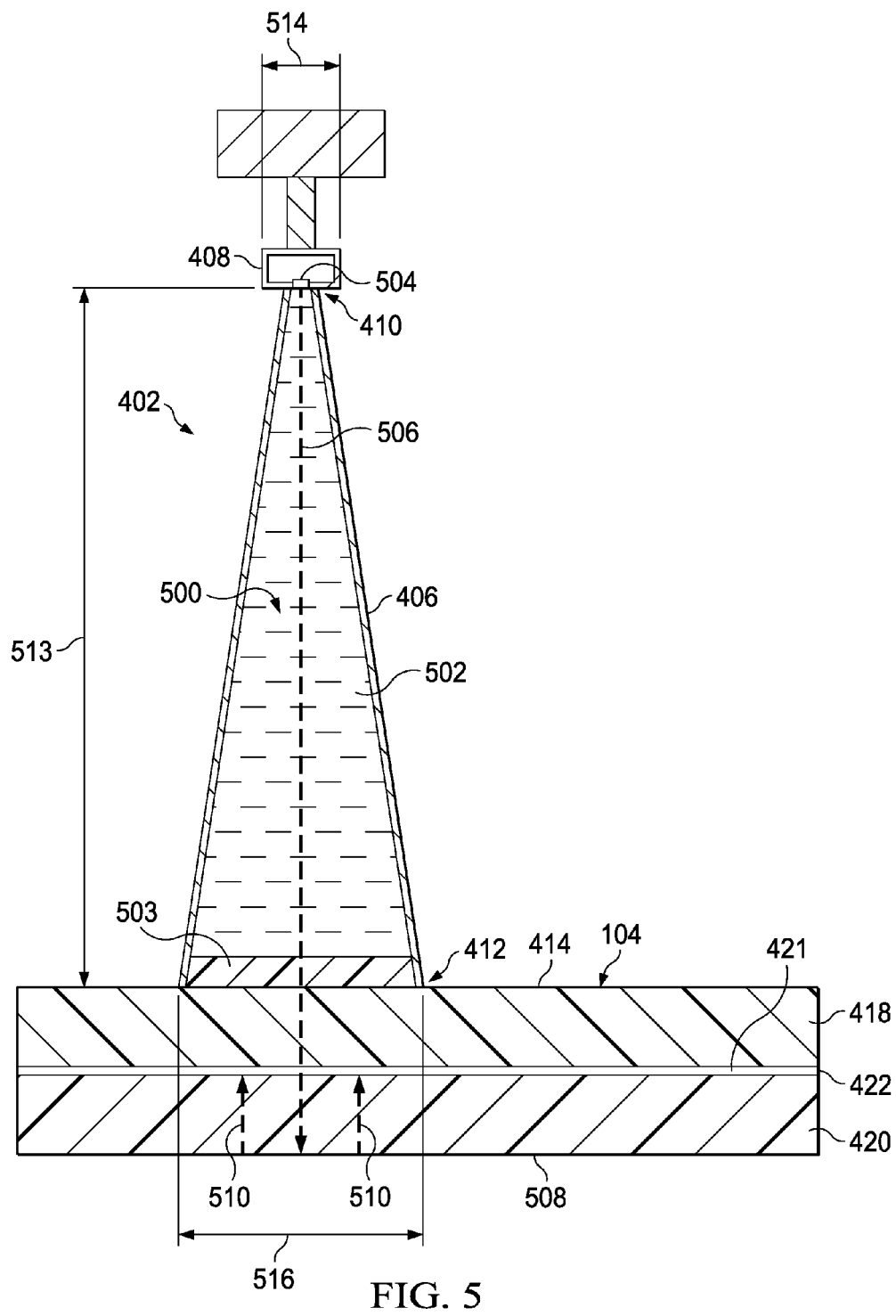
FIG. 5 is an illustration of a cross-sectional view of a portion of an inspection environment in accordance with an illustrative embodiment.

With reference now to FIG. 5, an illustration of a cross-sectional view of a portion of an inspection environment is depicted in accordance with an illustrative embodiment. In this illustrative example, a cross-sectional view of some components in inspection environment 400 in FIG. 4 is seen taken along lines 5-5.

In this cross-sectional view, cavity 500 of tube 406 is shown. Cavity 500 is an example of a physical implementation for cavity 302 shown in block form in FIG. 3. As can be seen, fluid 502 is present in cavity 500. In this example, fluid 502 takes the form of water. Of course, other types of fluids may be used depending on the particular implementation.

As depicted, plug 503 is associated with second end 412. Plug 503 is a structure that is configured to hold fluid 502 within cavity 500 when second end 412 of tube 406 is placed against surface 414 of skin panel 104. In these illustrative examples, plug 503 may take various forms. As depicted, plug 503 seals second end 412. In other illustrative examples, plug 503 may be a gasket that generates a seal when second end 412 is placed against surface 414 of skin panel 104.

In this illustrative example, energy source 408 is a hardware device and is configured to generate stress wave 506. In these illustrative examples, energy source 408 may generate energy in the form of an explosion or shockwave for a duration that is short enough to cause stress wave 506. In this illustrative example, energy source 408 includes capacitor 504. As depicted, capacitor 504 is in contact with fluid 502.

When capacitor 504 is discharged, the energy from the discharge results in the generation of stress wave 506. Stress wave 506 travels through fluid 502 within cavity 500 into the test object, which is skin panel 104 in this illustrative example. When plug 503 seals cavity 500, plug 503 also may function as a coupler for stress wave 506. When plug 503 performs this function, the selection of materials for plug 503 may be selected to have an acoustic impedance close to tube 406. In other words, the selection of the material and shape of plug 503 may be selected to reduce reflection of stress wave 506.

In this illustrative example, stress wave 506 travels through skin panel 104 until stress wave 506 reaches a feature. In this illustrative example, the feature is back surface 508. At back surface 508, tension wave 510 occurs during reflection of stress wave 506. Tension wave 510 subjects bond 421 at bond line 422 to tensile stress in this illustrative example. In other words, tension wave 510 causes tension that pulls first composite structure 418 and second composite structure 420 away from each other.

In this illustrative example, the configuration of tube 406 with cavity 500 is selected to set properties for stress wave 506. For example, the shape of tube 406 may be designed to focus the wave at a desired depth within skin panel 104, such as at the depth where bond 421 is located. This wave may be at least one of a stress wave or a tensile wave. This focusing of the wave may optimize the inspection method by maximizing the stress at the location of interest, reducing the likelihood of unintended occurrences of undesired inconsistencies to the test object in regions away from the bond to be inspected.

In this illustrative example, wave generator 402 has height 513. Wave generator 402 has width 514 at first end 410 and width 516 at second end 412. As depicted, height 513 may be about several centimeters, width 514 may be about a few centimeters, and width 516 may be about 1 centimeter. Of course these dimensions may vary depending on the particular implementation. The dimension selected may vary depending on the particular implementation. In these illustrative examples, dimensions may be selected such that wave generator 402 may be easily positioned on different parts to provide a desired inspection of bonds in those parts.

Figure 6:
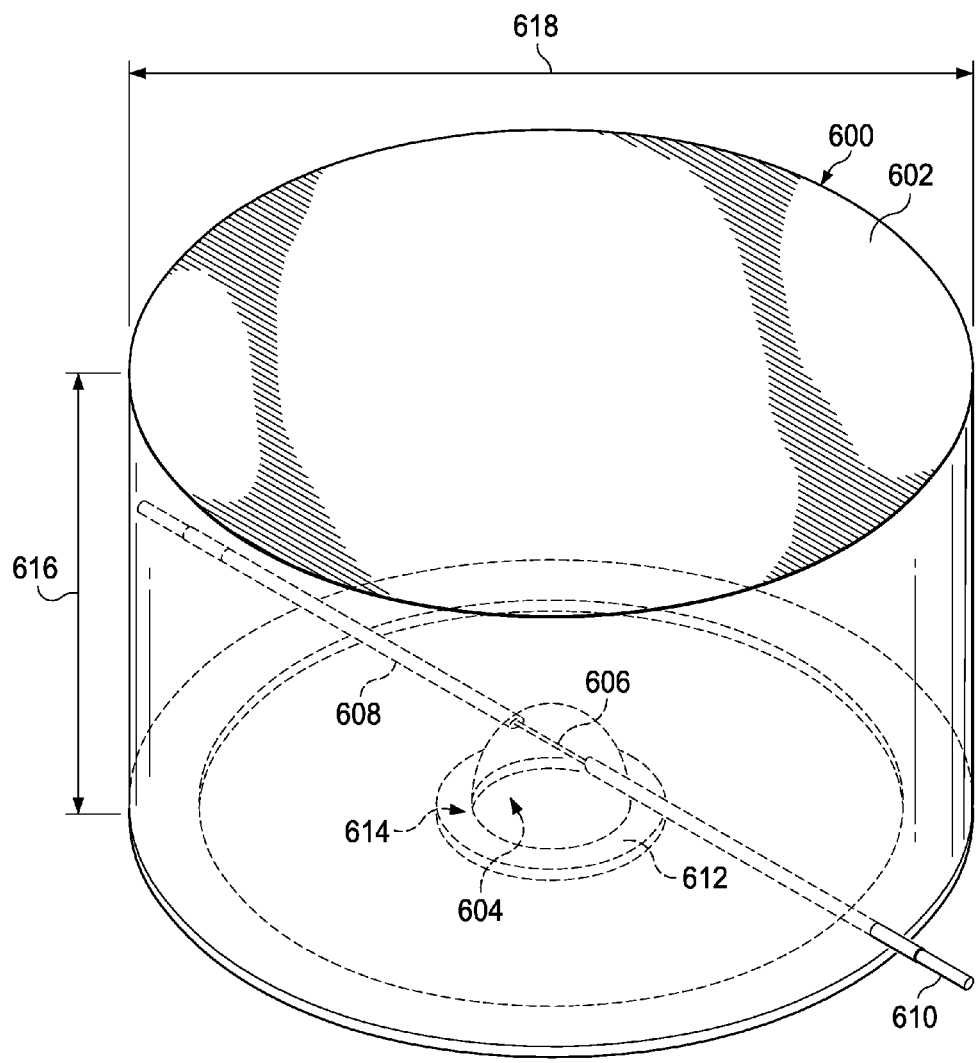
FIG. 6 is an illustration of a wave generator in accordance with an illustrative embodiment.

Turning now to FIG. 6, an illustration of a wave generator is depicted in accordance with an illustrative embodiment. As depicted, wave generator 600 is another example of an implementation for wave generator 314 shown in block form in FIG. 3. Wave generator 600 comprises structure 602 having a cylindrical shape rather than a tube as depicted for wave generator 402 in FIG. 4.

In this illustrative example, cavity 604 can be seen in phantom within structure 602. As can be seen in this example, cavity 604 has an egg shape. This configuration of structure 602 is another example of another physical implementation for cavity 302 shown in block form in FIG. 3.

Wire 606 extends through structure 602 into cavity 604. Wire 606 is connected to wire 608 and wire 610. Wire 608 and wire 610 are thicker than wire 606. Wire 606 is an example of an implementation for energy source 304 shown in block form in FIG. 3. Wire 606 is an exploding bridge wire which explodes when a current flows through wire 606. This explosion is configured to generate a stress wave in a fluid within cavity 604.

Also shown in phantom is gasket 612. Gasket 612 is configured to seal cavity 604 at end 614 of cavity 604.

As depicted, structure 602 has height 616 and diameter 618. Height 616 may be about 3.7 centimeters, and diameter 618 may be about 7 centimeters in this illustrative example.

Figure 7:
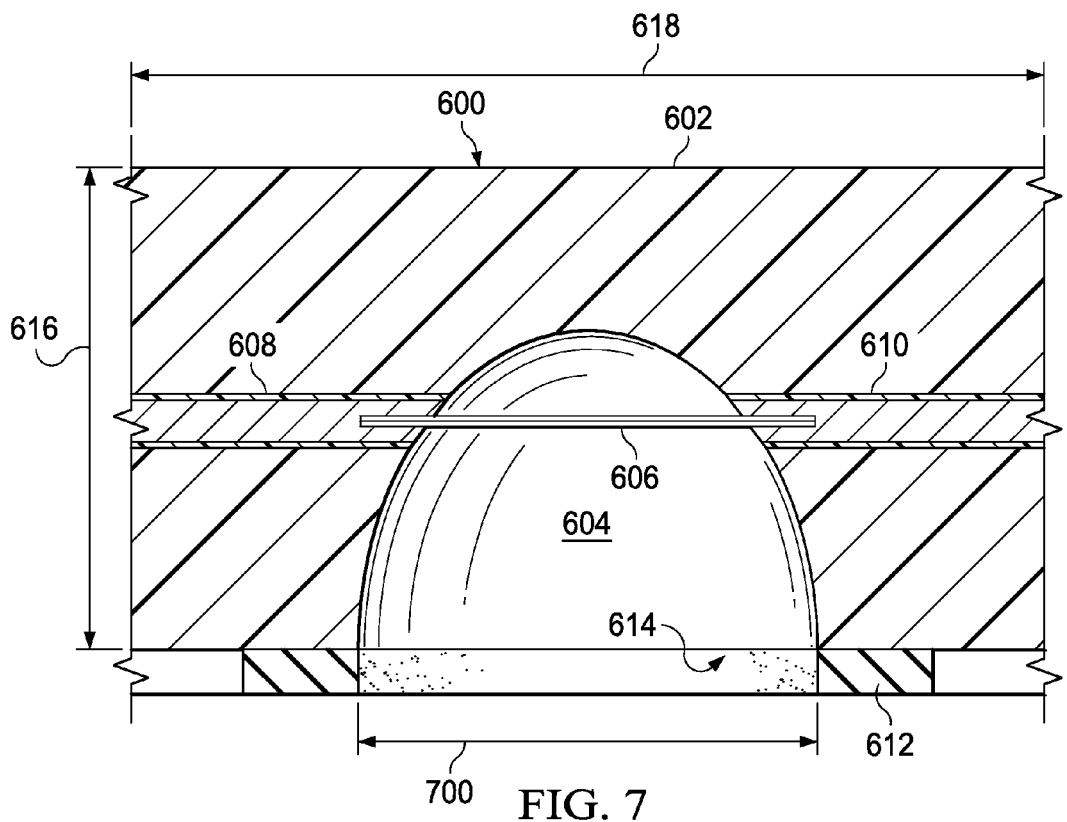
FIG. 7 is an illustration of a cross-sectional view of a portion of a wave generator in accordance with an illustrative embodiment.

With reference now to FIG. 7, an illustration of a cross-sectional view of a portion of wave generator 600 is depicted in accordance with an illustrative embodiment. A larger view of cavity 604, wire 606, and gasket 612 can be seen. In particular, end 614 of cavity 604 has diameter 700. Diameter 700 is about 1 centimeter in this illustrative example.

Figure 8:
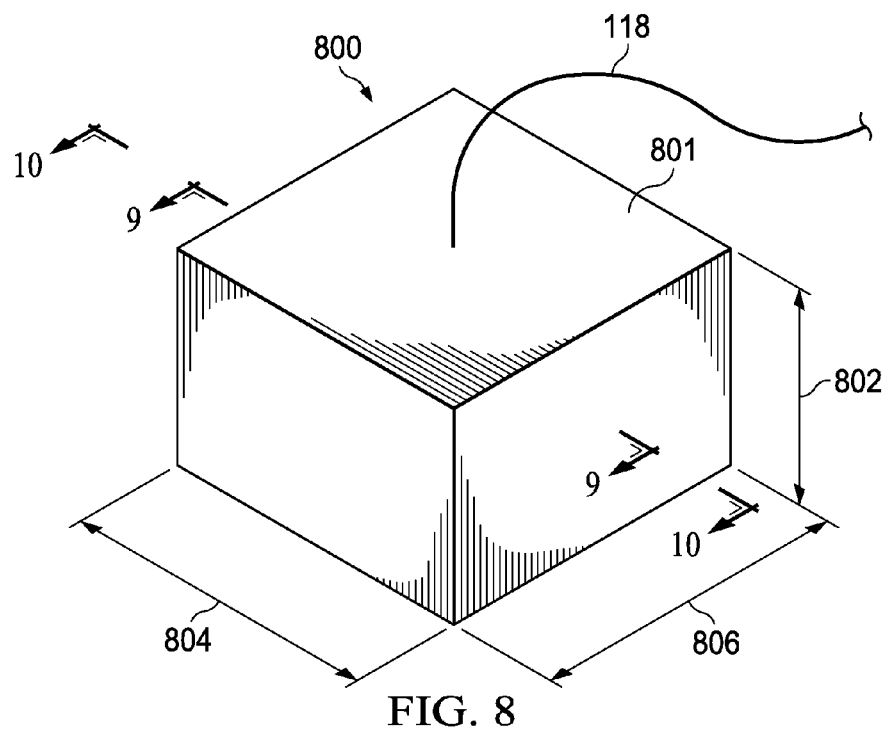
FIG. 8 is an illustration of a wave generator in accordance with an illustrative embodiment.

Turning now to FIG. 8, an illustration of a wave generator is depicted in accordance with an illustrative embodiment. In this illustrative example, wave generator 800 is another example of a physical implementation for wave generator 314 shown in block form in FIG. 3.

In this illustrative example, wave generator 800 has structure 801. Structure 801 has a cuboid shape. In this particular example, structure 801 has height 802, depth 804, and width 806. In this illustrative example, height 802 is about 1 centimeter, depth 804 is about 2 centimeters, and width 806 is about 2 centimeters. Of course, the values for these dimensions are only examples of one set of dimensions for height 802, depth 804, and width 806. Other values for these dimensions may be used in other illustrative implementations.

Figure 9:
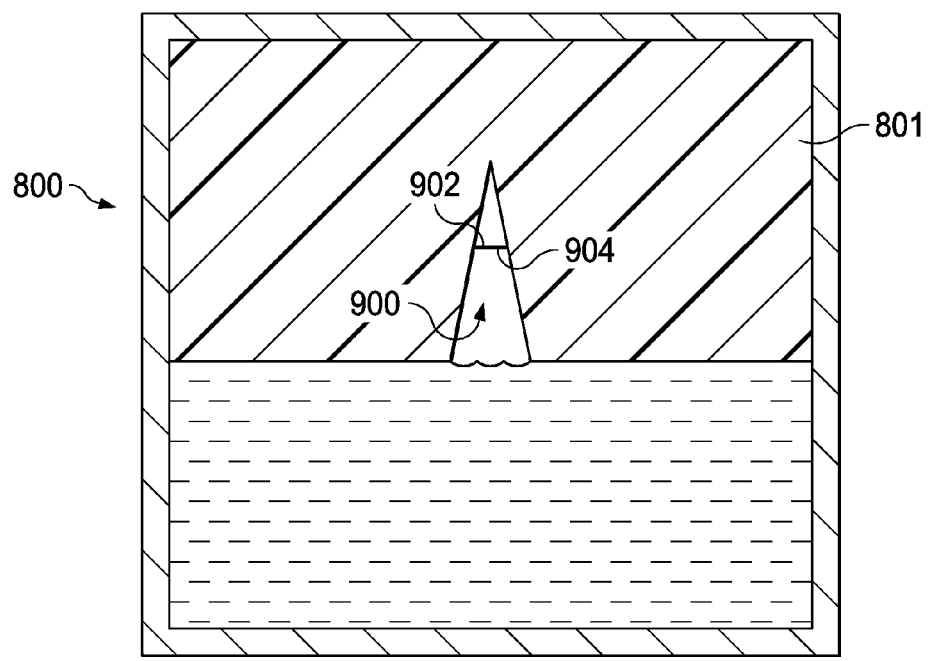
FIG. 9 is an illustration of a cross-sectional view of a wave generator in accordance with an illustrative embodiment.

Turning next to FIG. 9, an illustration of a cross-sectional view of a wave generator is depicted in accordance with an illustrative embodiment. In this illustrative example, a cross-sectional view of structure 801 is shown taken along lines 9-9 in FIG. 8.

In this illustrative example, cavity 900 has a conical shape. Energy source 902 takes the form of wire 904. Wire 904 is configured to explode when a current is applied to wire 904. This explosion is configured to generate a stress wave in a fluid within cavity 900.

Figure 10:
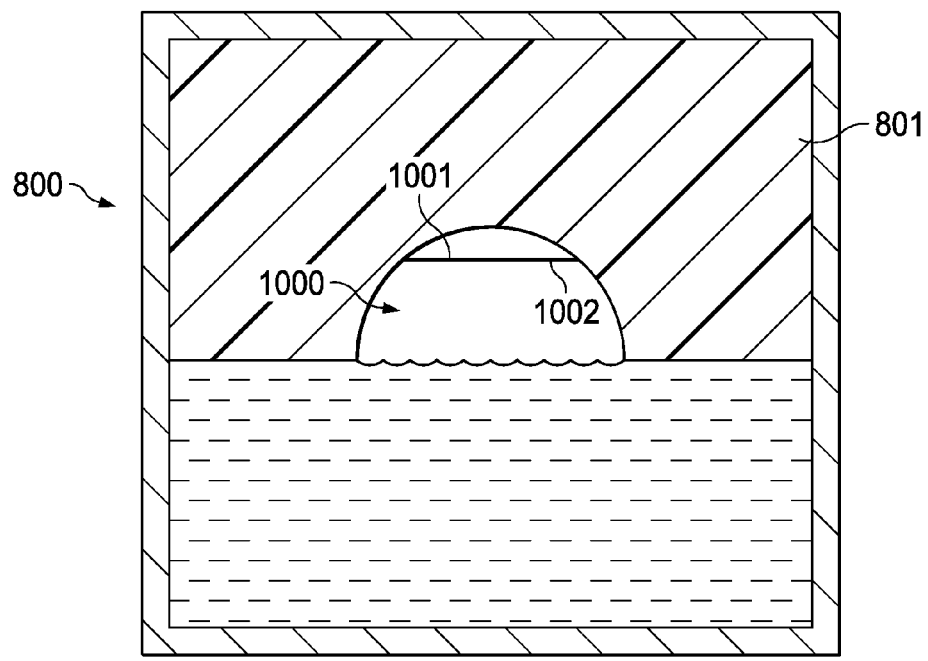
FIG. 10 is an illustration of another cross-sectional view of a wave generator in accordance with an illustrative embodiment.

With reference now to FIG. 10, an illustration of another cross-sectional view of a wave generator is depicted in accordance with an illustrative embodiment. In this illustrative example, an alternate cross-sectional view of structure 801 is shown taken along lines 10-10.

In this cross-sectional view, cavity 1000 has a hemispherical shape. Energy source 1001 is wire 1002 in this example.

The different components shown in FIG. 1 and FIGS. 4-10 may be combined with components in FIGS. 2-3, used with components in FIGS. 2-3, or a combination of the two. Additionally, some of the components in FIG. 1 and FIGS. 4-10 may be illustrative examples of how components shown in block form in FIGS. 2-3 can be implemented as physical structures.

Figure 11:
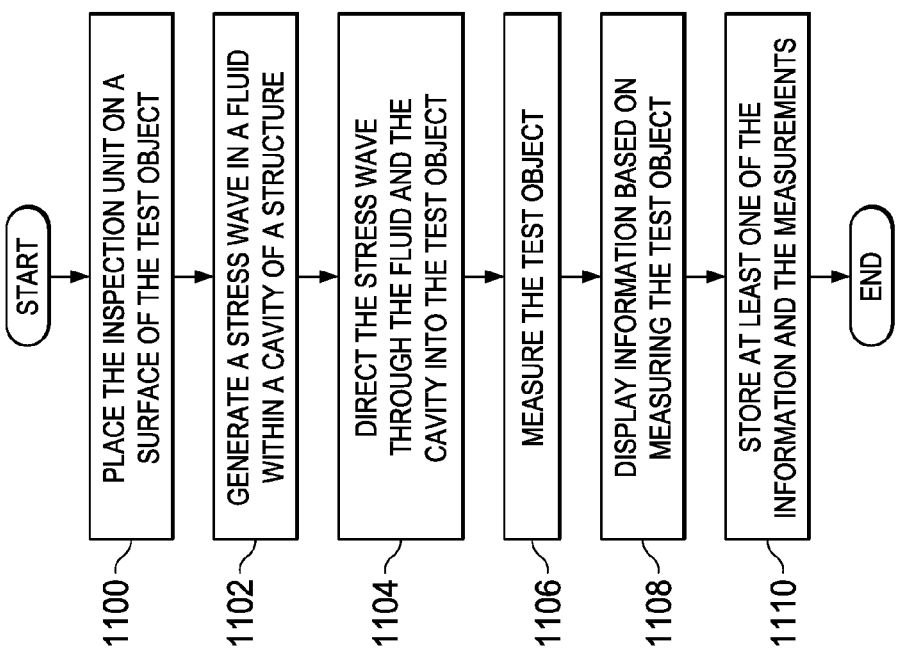
FIG. 11 is an illustration of a flowchart of a process for inspecting a test object in accordance with an illustrative embodiment.

Turning next to FIG. 11, an illustration of a flowchart of a process for inspecting a test object is depicted in accordance with an illustrative embodiment. The process illustrated in FIG. 11 may be implemented in inspection environment 200 in FIG. 2. In particular, the process may be implemented to inspect test object 204 using inspection unit 230.

The process begins by placing the inspection unit on a surface of the test object (operation 1100). The process then generates a stress wave in a fluid within a cavity of a structure (operation 1102). The process then directs the stress wave through the fluid and the cavity into the test object (operation 1104). A number of properties for the stress wave in the fluid is set based on the configuration of the cavity in the structure. These properties are set as the stress wave travels through the fluid in the cavity. As a result, the stress wave causes a tension wave that encounters a bond in the test object. In the illustrative example, the tension wave that encounters the test object may be the tension wave caused by the stress wave reflecting from an interface such as a back wall. Further, in some illustrative examples, the tension wave also may be a component of the stress wave that encounters the bond as the stress wave travels towards the interface.

Measurements are made of the test object (operation 1106). In operation 1106, the measurements may be performed using any device configured to detect inconsistencies that may occur from the bond carrying the load caused by the tensile forces that may be applied by the tension wave. In one illustrative example, a laser interferometer is used to determine whether inconsistencies are present after the stress wave travels through the test object and causes a tension wave to apply a load on the bond. Information based on measuring the test object is displayed (operation 1108). The process also stores at least one of the information and the measurements (operation 1110), with the process terminating thereafter.

These operations may be used to determine whether the bond in the test object can withstand loads within a desired amount or range. These different operations may be repeated any number of times. The operations may be repeated for different locations on a particular test object or on different test objects.

Figure 12:
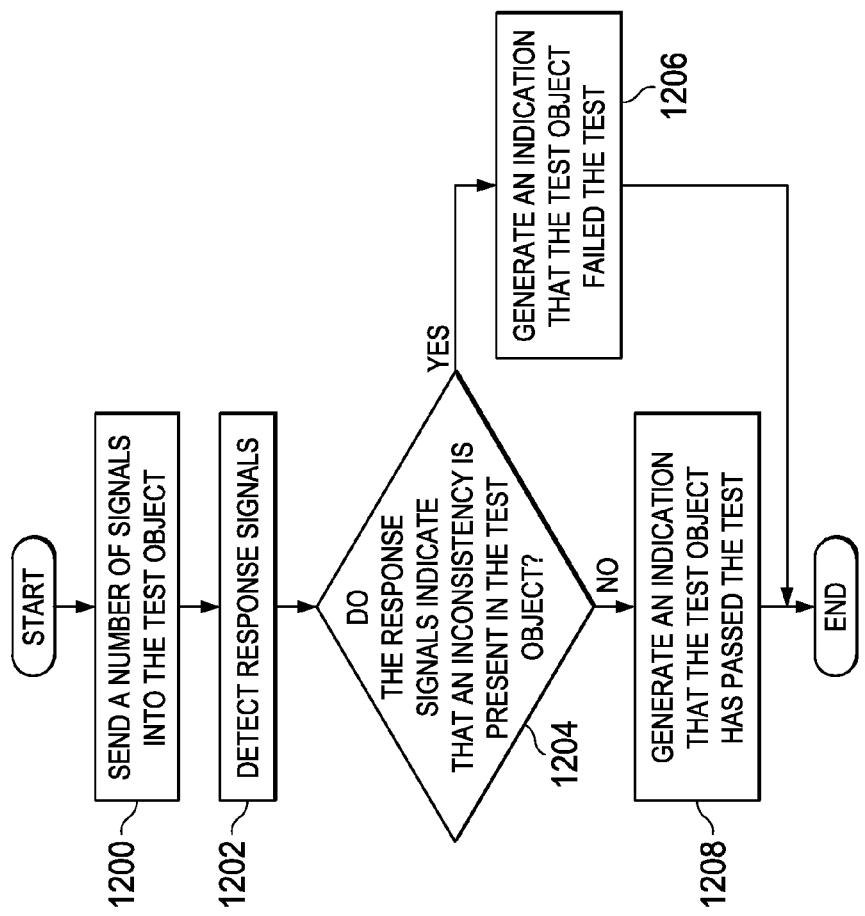
FIG. 12 is an illustration of a flowchart of a process for testing a test object in accordance with an illustrative embodiment.

With reference now to FIG. 12, an illustration of a flowchart of a process for testing a test object is depicted in accordance with an illustrative embodiment. This process may be implemented after a tension wave has been sent through a test object. The process illustrated in FIG. 12 may be implemented using inspection system 202 in FIG. 2.

The process begins by sending a number of signals into the test object (operation 1200). These signals may be sent using an ultrasonic transducer.

The process then detects response signals (operation 1202). A determination is then made as to whether the response signals indicate that an inconsistency is present in the test object (operation 1204). If an inconsistency is present, an indication is generated that the test object failed the test (operation 1206), with the process terminating thereafter.

With reference again to operation 1204, if an inconsistency is not present, the process generates an indication that the test object has passed the test (operation 1208), with the process terminating thereafter. In this case, the bond in the test object has held up to the forces generated on the bond by the tension waves. As a result, this test object may be certified as withstanding the force selected for testing.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, operation 1108 and operation 1110 are optional operations and may be omitted. Further, in other illustrative examples, an alert may be generated if a determination is made from the measurement of the different waves that the bond does not have a desired strength. Additionally, other types of measurement systems may be used depending on the particular implementation.

Figure 13:
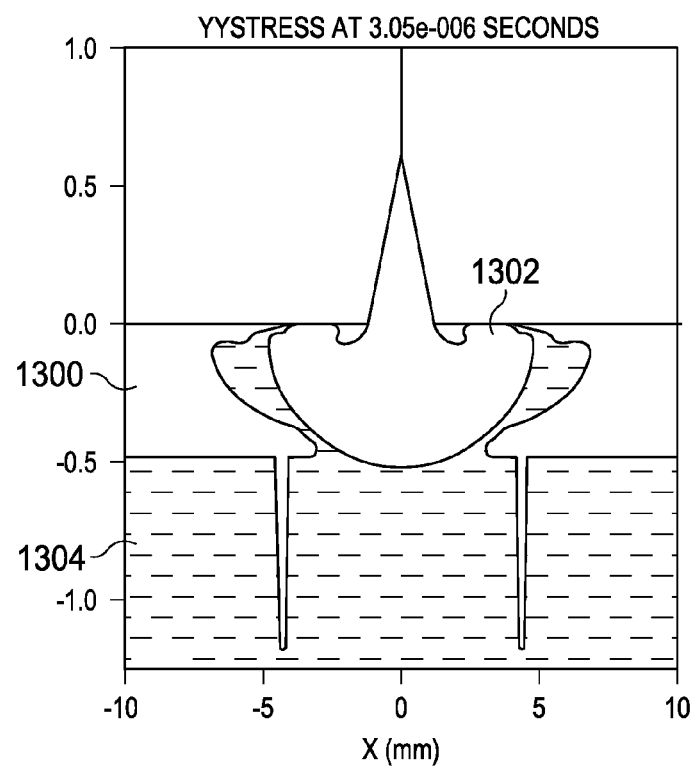
FIG. 13 is an illustration of a discharge of energy in a wave generator in accordance with an illustrative embodiment.
Figure 13:
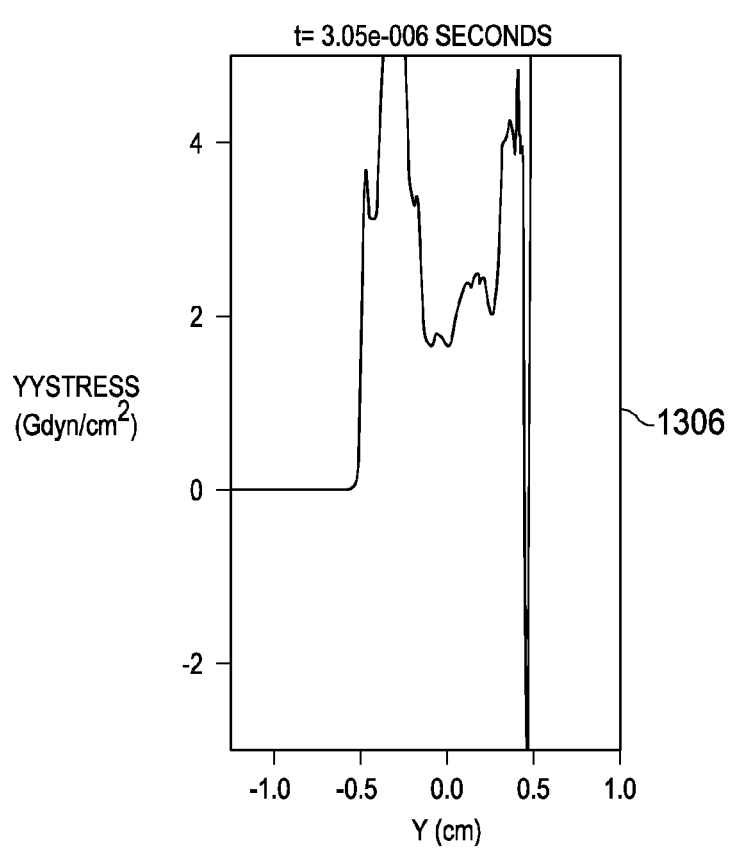

Turning now to FIG. 13, an illustration of a discharge of energy in a wave generator is depicted in accordance with an illustrative embodiment. In this illustrative example, graph 1300 illustrates shape 1302 of a stress wave that is discharged into fluid 1304. This stress is shown at a time of about 3.05×10 006 seconds after energy discharge.

Graph 1306 shows the stress in $Gdyn/cm^2$. In this illustrative example, 1 $Gdyn/cm^2$ is a measure of stress equivalent to 1 kilobar, or 1000 atm. As can be seen, the stress wave generated may be focused at a specific depth in a test object based on the configuration of the cavity. By varying the shape of the cavity, the focal point of the stress wave may be changed. This focal point may be at different locations such as at an interface, a back wall of an object, the bond line, or some other location depending on the particular implementation. The depth of the focal point may be selected to provide a desired testing of the bond line.

Figure 14:
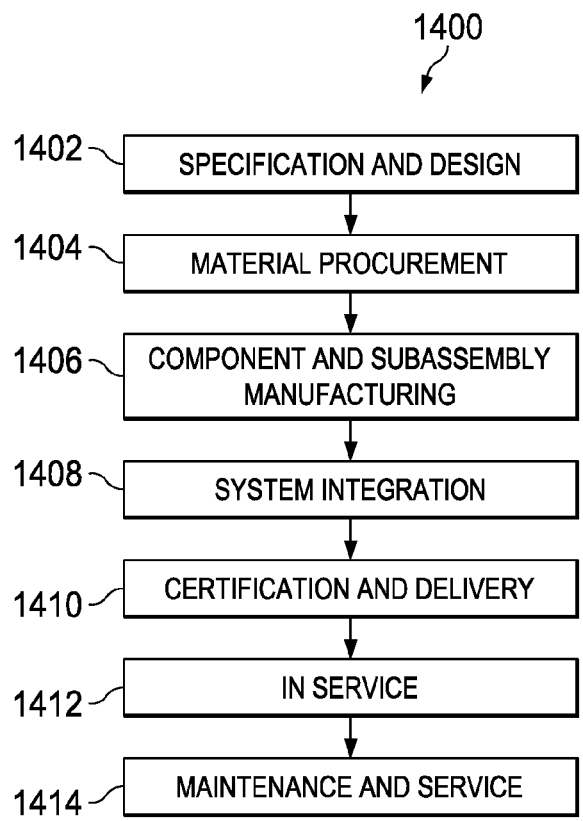
FIG. 14 is an illustration of a block diagram of an aircraft manufacturing and service method in accordance with an illustrative embodiment.
Figure 15:
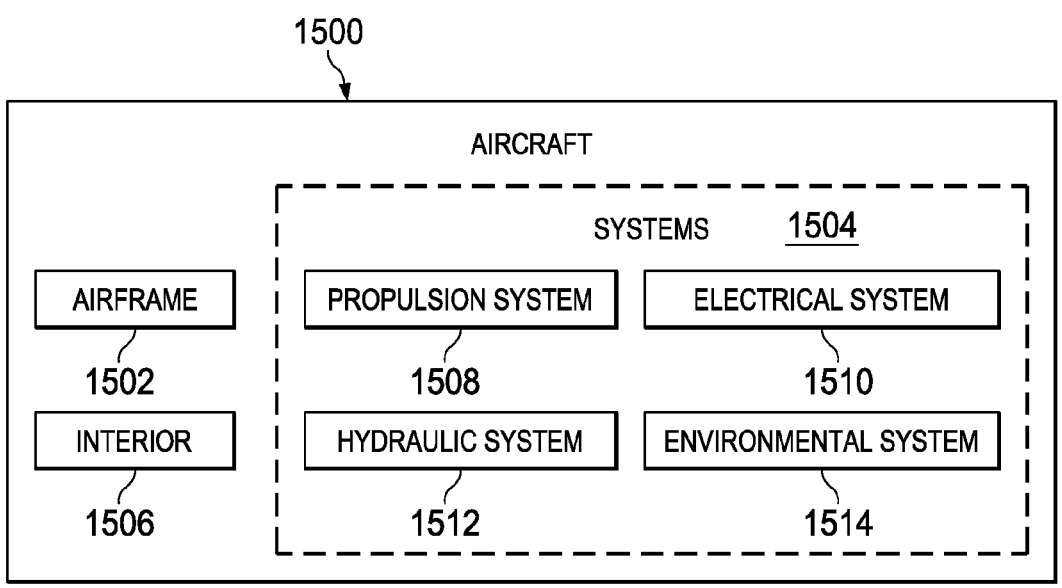
FIG. 15 is an illustration of a block diagram of an aircraft in which an illustrative embodiment may be implemented.

Illustrative embodiments of the disclosure may be described in the context of aircraft manufacturing and service method 1400 as shown in FIG. 14 and aircraft 1500 as shown in FIG. 15. Turning first to FIG. 14, an illustration of a block diagram of an aircraft manufacturing and service method is depicted in accordance with an illustrative embodiment. During pre-production, aircraft manufacturing and service method 1400 may include specification and design 1402 of aircraft 1500 in FIG. 15 and material procurement 1404.

During production, component and subassembly manufacturing 1406 and system integration 1408 of aircraft 1500 in FIG. 15 takes place. Thereafter, aircraft 1500 in FIG. 15 may go through certification and delivery 1410 in order to be placed in service 1412. While in service 1412 by a customer, aircraft 1500 in FIG. 15 is scheduled for routine maintenance and service 1414, which may include modification, reconfiguration, refurbishment, and other maintenance or service.

Each of the processes of aircraft manufacturing and service method 1400 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 15, an illustration of a block diagram of an aircraft is depicted in which an illustrative embodiment may be implemented. In this example, aircraft 1500 is produced by aircraft manufacturing and service method 1400 in FIG. 14 and may include airframe 1502 with systems 1504 and interior 1506. Examples of systems 1504 include one or more of propulsion system 1508, electrical system 1510, hydraulic system 1512, and environmental system 1514. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1400 in FIG. 14.

For example, the illustrative embodiments may be implemented to inspect the bonds in test objects such as aircraft parts during component and subassembly manufacturing 1406. Further, different parts may be tested using an illustrative embodiment after or during installation of those parts as part of system integration 1408. Further tests of parts may be made during certification and delivery 1410. As another illustrative example, parts may be tested during maintenance and service 1414. This testing may be performed on parts that may be inspected during maintenance and service 1414. Further, parts may be tested using an illustrative embodiment for use in maintenance, upgrades, refurbishment, or other operations performed during maintenance and service 1414.

Thus, the illustrative embodiments provide a method and apparatus for testing bonds in objects. In these illustrative examples, the wave generator may have a size that is smaller than currently used in inspection systems such as laser bond inspection systems. The size of the wave generator in these illustrative examples may allow for testing of parts that have configurations or shapes that are more difficult for inspection with laser bond inspection systems. Further, the size of the wave generator in these illustrative examples may allow for inspections of objects, such as parts that have been installed in a structure such as an aircraft, a train, a building, a manufacturing facility, or some other type of structure.

The illustrative embodiments allow for the stress wave to have a number of properties such as magnitude of the stress wave, duration of the stress wave, a rise time for the stress wave, a focal point, and other suitable properties that may be set based on the configuration of the wave generator. In this manner, the different illustrative embodiments provide that wave generators may be used to test various bond strengths for bonds that may be in different locations in a test object.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for testing a test object, the method comprising:
   generating, via a wire at a first end of a structure, a stress wave within a cavity in the structure, wherein a surface of the test object is coupled to a second end of the structure opposite the first end of the structure, and wherein the wire is an exploding bridge configured to explode when a current flows through the wire;
   setting a number of properties for the stress wave in a fluid within the cavity based on a configuration of the cavity, wherein the number of properties comprise a depth within the test object from the surface of the test object at which the stress wave is focused in the test object; and directing the stress wave through the cavity into the test object to the depth within the test object.

2. The method of claim 1, wherein the number of properties further comprises a magnitude of the stress wave, a duration of the stress wave, or a rise time for the stress wave.

3. The method of claim 1, wherein the directing step comprises:
directing the stress wave through a fluid within the cavity into the test object, wherein a tension wave occurs and encounters a bond in the test object.

4. The method of claim 3 further comprising:
measuring the test object.

5. The method of claim 4 further comprising:
displaying information based on measurements of the test object.

6. The method of claim 4 further comprising:
storing at least one of information or measurements of the test object.

7. The method of claim 1, wherein the structure is a tube having the first end and the second end.

8. The method of claim 1, wherein the cavity is filled with the fluid, and the stress wave is generated by a hydroshock technique.

9. The method of claim 1, wherein the cavity has a cross-sectional shape of a cone.

10. An apparatus comprising:
an energy source comprising a wire at a first end of a structure, wherein the wire is an exploding bridge configured to explode when a current flows through the wire; and
the structure having a cavity, wherein the energy source is configured to generate a stress wave that travels through the cavity into a test object having a surface coupled to a second end of the structure opposite the first end of the structure, wherein the structure is configured to set a number of properties for the stress wave in a fluid within the cavity based on a configuration of the cavity in the structure, and wherein the number of properties comprises a depth within the test object from the surface of the test object at which the stress wave is focused in the test object.

11. The apparatus of claim 10, wherein the number of properties further comprises a magnitude of the stress wave, a duration of the stress wave, or a rise time for the stress wave.

12. The apparatus of claim 10, wherein the structure is configured to direct the stress wave through the fluid within the cavity into the test object such that a tension wave occurs and encounters a bond in the test object.

13. The apparatus of claim 10 further comprising:
a measurement system configured to measure the test object.

14. The apparatus of claim 13, wherein the measurement system comprises:
a laser interferometer.

15. The apparatus of claim 13, wherein the measurement system is configured to store at least one of information or measurements of the test object.

16. The apparatus of claim 13 further comprising:
a display system configured to display information about the test object measured by the measurement system.

17. The apparatus of claim 16, wherein the display system is selected from one of an oscilloscope, a tablet computer, a notebook computer, or a workstation.

18. The apparatus of claim 10, wherein the structure comprises:
a tube having the first end and the second end.

19. The apparatus of claim 18 further comprising:
a plug configured to be associated with the second end and to hold the fluid within the cavity.

* * * * *